United States Patent [19]

Quentin-Millet et al.

[11] Patent Number: 4,965,205

[45] Date of Patent: Oct. 23, 1990

[54] CULTURE MEDIUM FOR BACTERIA OF THE BORDETELLA GENUS CONTAINING ETHERIFIED DERIVATIVE OF D-GLUCOSE AND A CYCLODEXTRIN

[75] Inventors: Marie-José B. Quentin-Millet, Villeurbanne; François Arminjon; Roupen R. Donikian, both of Lyons, all of France

[73] Assignee: Institut Merieux, Lyons, France

[21] Appl. No.: 364,367

[22] Filed: Jun. 12, 1989

Related U.S. Application Data

[63] Continuation-in-part of Ser. No. 31,054, Mar. 27, 1987, abandoned.

[51] Int. Cl.$^5$ .................. C12N 1/12; C12N 1/22; C12N 1/20
[52] U.S. Cl. .................. 435/252; 435/253.6; 435/244; 435/252.1; 435/248; 435/822
[58] Field of Search .................. 435/253.6, 252, 244, 435/248, 822, 252.1

[56] References Cited

U.S. PATENT DOCUMENTS 4,500,639  2/1985  Suzuki et al. .................. 435/822
4,849,358  7/1989  Chazono et al. .................. 435/252

Primary Examiner—Ronald W. Griffin
Assistant Examiner—Pamela S. Webber
Attorney, Agent, or Firm—Cushman, Darby & Cushman

[57] ABSTRACT

A culture medium composition for bacteria of the Bordetella genus comprises a nutrient medium containing cyclodextrin or a salt thereof in combination with an etherified derivative of D-glucose polymer having a molecular mass at least equal to 2,000. A process for culturing bacteria of the Bordetella genus with such a medium is also disclosed.

11 Claims, 2 Drawing Sheets

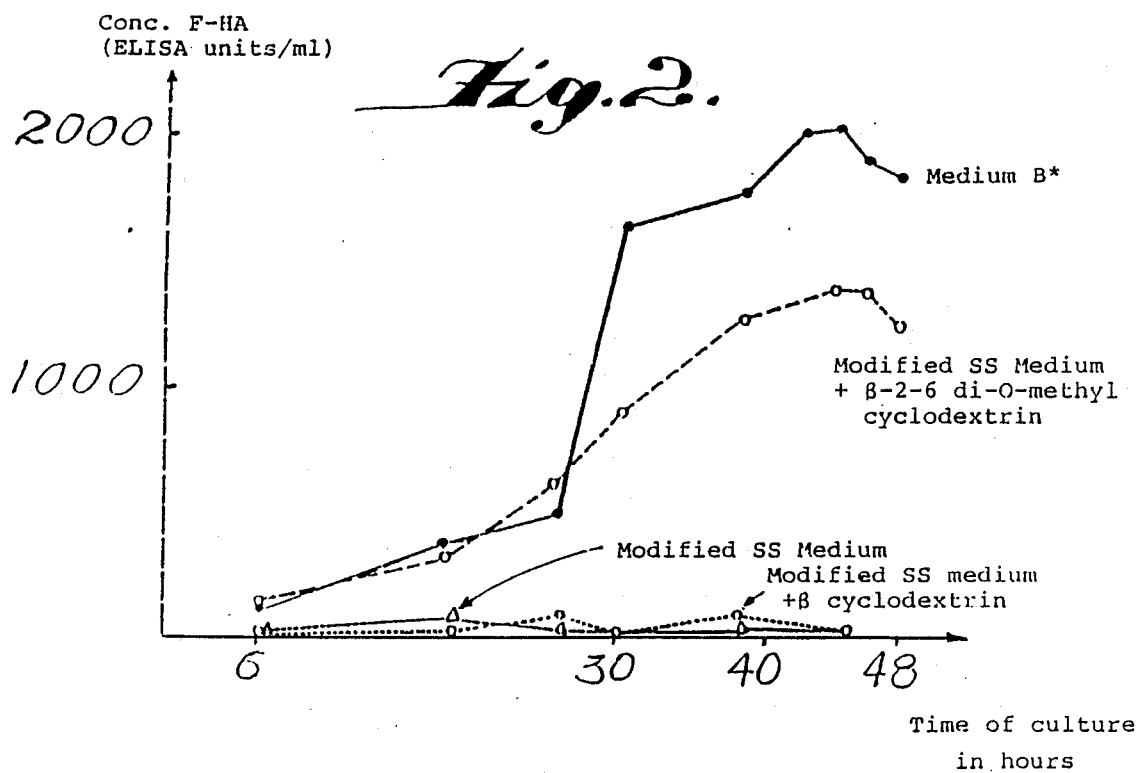
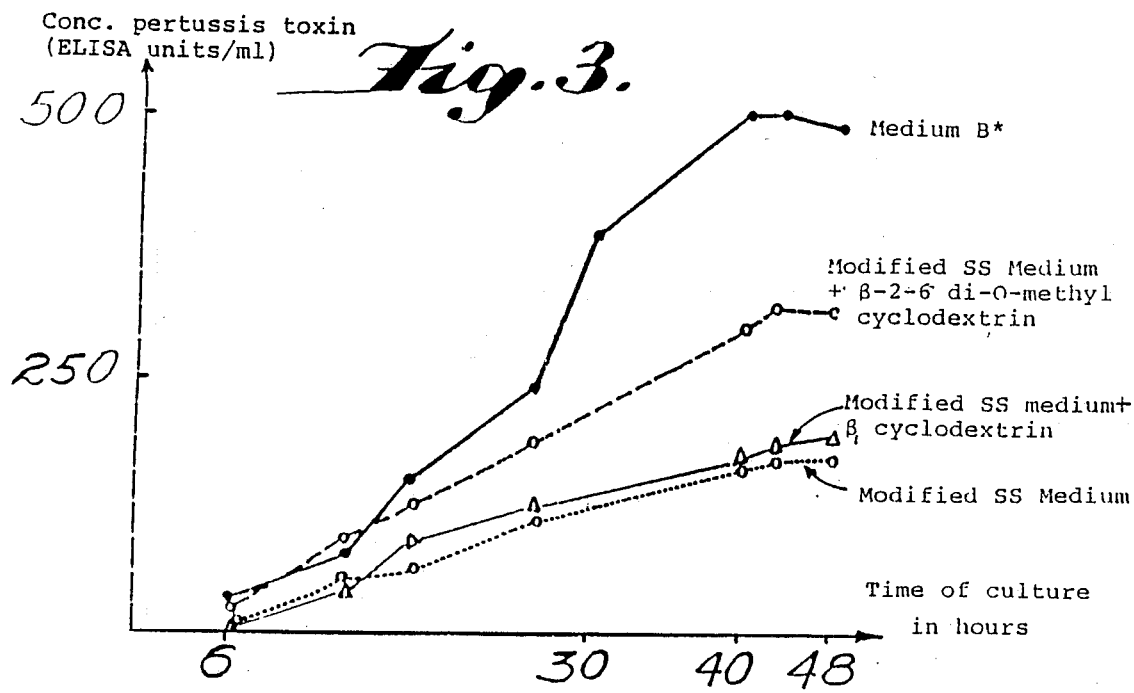
* Medium B: Modified SS + β cyclodextrin + methylcellulose

CULTURE MEDIUM FOR BACTERIA OF THE BORDETELLA GENUS CONTAINING ETHERIFIED DERIVATIVE OF D-GLUCOSE AND A CYCLODEXTRIN

This application is a continuation-in-part of our application Ser. No. 07/031,054, filed Mar. 27, 1987, now abandoned The present invention relates to a new culture medium composition for bacteria belonging to the Bordetella type, this culture medium containing at least one etherified derivative of D-glucose polymer. The invention also concerns a method for culturing said bacteria using such a medium.

It is known that the bacteria culture of the Bordetella genus, for example, *Bordetella pertussis, Bordetella parapertussis* and *Bordetella bronchiseptica*, cause difficult problems, principally in perfecting a purely synthetic culture medium.

The *Bordetella pertussis* bacteria is a pathogenic agent of whooping cough, and its industrial culture is necessary to produce acellular anti-whooping cough vaccines or whole germs.

It is also known that the culture of *Bordetella pertussis* phase I provides in the culture medium pertussis toxin (also called LPF or LPF-HA: Leukocytosis Promoting Factor—Hemagglutinin) and F-HA (Filamentous Hemagglutinin) which are antigenic substances capable of entering into the composition of an acellular anti-whooping cough vaccine.

The bacteria of the Bordetella genus were initially cultivated on a solid medium called a Bordet-Gengou medium.

One liquid medium for the culture of *Bordetella pertussis* bacteria phase I has been described by J. W. Hornibrook, Public Health Reports, 54, No. 41, 1847–1851 (1939). The medium described by Hornibrook contains starch. Hornibrook has pointed out, moreover, that it is possible to replace the starch with $\beta$-dextrin or $\alpha$-dextrin. These dextrins, now called $\alpha$- and $\beta$-cyclodextrin, are polyosides obtained by the action of *B. macerans* on potato starch.

Several authors have then modified and improved the medium described by Hornibrook, and a purely synthetic liquid medium has been perfected by Stainer and Scholte, J. Gen. Microbiol., 63 211–220 (1970).

The culture medium of Stainer and Scholte, currently called an SS medium, is chemically defined. It is devoid of natural substances or their derivatives, such as yeast extracts, polypeptones and the like.

The absence of such complex substances in the medium renders more easy the purification of protein antigens excreted by microorganisms, such as pertussis toxin and F-HA. The SS medium also provides good reproducibility of the quality of the germ suspension obtained at the end of the culture.

The SS medium contains, essentially, in defined amounts, the following products: sodium glutamate, L-proline, sodium chloride, potassium dihydrogenphosphate, potassium chloride, magnesium chloride, calcium chloride, tris-hydroxymethylamino methane, to which the following products are added: L-cystine, ferrous sulfate, ascorbic acid, glutathione of the reduced type and niacin.

In a modified SS medium there is also added a solution of casamino-acids or corresponding peptides.

However, the SS medium does not permit expression of antigens already cited in an amount sufficiently compatible with industrial development. Moreover, with this liquid medium, the F-HA antigen can be produced only when the culture is carried out under static conditions.

To produce pertussis toxin and F-HA in the stirred or shaken liquid medium, Imaizumi et al., J. Clin. Microbiol. 17, No. 5, 781–786 (1983), have defined a modified Stainer and Scholte medium in which they have added a methyl derivative of $\beta$-cyclodextrin. This cyclic polyoside, also called heptakis (2,6-0-dimethyl) $\beta$-cyclodextrin, increases both the biomass and the production of pertussis toxin and F-HA.

However, the use of this methyl derivative of $\beta$-cyclodextrin raises economic problems because of the step of preparing the dimethyl derivative in the 2,6 position starting with $\beta$-cyclodextrin, by enzymatic reaction.

Thus, one embodiment of the present invention relates to a culture medium composition based on chemically defined compounds which is capable of assisting the development of bacteria of the Bordetella genus, and in particular, assisting the simultaneous production of pertussis toxin antigens and F-HA with a high yield. This new culture medium thus can avoid the costly use of etherified derivatives of cyclodextrin.

It has now been discovered that while the etherified derivatives of D-glucose polymers, having a molecular mass at least equal to 2,000, have no effect either on the production of pertussis toxin or on the production of F-HA, and even inhibit the growth of cultures of the Bordetella genus, that nonetheless, in a surprising manner, these etherified derivatives, when combined with cyclodextrin or a derivative thereof assist the microbial development and/or simultaneous production of pertussis toxin and F-HA in a high yield.

The present invention thus also related to a new culture medium composition for bacteria of the Bordetella genus, comprising basal components necessary for this culture, as well as cyclodextrin or its derivatives, said composition also containing at least one etherified derivative of a D-glucose polymer whose molecular mass is at least equal to 2,000.

The D-glucose polymers from which are derived the etherified products employed in the present invention, are polymers whose D-glucose units are joined by an $\alpha$-bond, as in amylose, of by a $\beta$-bond, as in cellulose.

Representative etherified derivatives of D-glucose polymers include, principally, the etherified derivatives of cellulose in which a portion of the hydroxyl groups are etherified by lower alkyl or lower hydroxyalkyl groups. Representative etherified derivatives of cellulose include, in particular, methyl cellulose, hydroxypropyl methylcellulose, hydroxyethyl cellulose, hydroxybutyl cellulose and the like; all these products are commercial products sold principally by Dow Chemical, Colorcon, Union Carbide and Hercules, Inc. Carboxymethyl cellulose which is also a commercial product, sold principally by Hercules Inc. or E. I. duPont de Nemours, can also be employed. Representative other etherified derivatives of D-glucose polymers include the corresponding derivatives of starch, and in particular amylose.

The upper limit of the molecular weight of the etherified derivatives of D-glucose polymers is not critical. Preferably, however, the etherified derivative is selected in such a manner that the molecular weight and the degree of substitution are such that the derivatives at the concentrations employed are soluble in water. Generally, the culture medium of the present invention contains from 0.01 to 2 g/liter of etherified derivative of D-glucose polymer, and preferably from 0.05 to 0.5 g/liter.

The etherified derivative can be added to the medium in several stages, generally from 2 to 6 stages. There is added, for example, at each stage, from 0.01 to 1 g/liter of said derivative.

The cyclodextrin (or one of its derivatives) is present in the culture medium of the present invention in an amount ranging from 0.5 to 5 g/liter, preferably from 1 to 2 g/liter.

The cyclodextrin can be α-cyclodextrin, β-cyclodexrin or γ-cyclodextrin. The cyclodextrin derivatives are principally the etherified derivatives.

The present invention also related to the use of the etherified derivatives of D-glucose polymers, such as defined above, in combination with cyclodextrin or its derivatives, in the culture of bacteria of the Bordetella genus, and in particular in the culture of a stirred or shaken medium of Bordetella pertussis, to assist the growth of the culture and/or the expression of pertussis toxin antigens and F-HA.

The present invention relates in particular, to a process for culturing bacteria of the Bordetella genus, using the culture medium composition described above. This process which comprises cultivating the said bacteria in an appropriate culture medium, the culture medium containing a cyclodextrin or a derivative thereof, is characterized by the fact that there is added to the said culture medium at least one etherified derivative of D-glucose-polymer, such as defined above.

The said etherified derivative of D-glucose polymer can be added all at once at the beginning of the culture, or in several stages, as indicated above, so as to employ from 0.05 to 2 g liter and preferably from 0.05 to 0.5g/liter, of said derivative.

There is described below a particular method of the present invention carried out in a stirred liquid medium.

Representative based culture media useful in the process of the present invention include principally an SS modified medium (medium I) having the following composition (per 1 liter):

| | |
|---|---|
| sodium glutamate | 10.72 g |
| L-proline | 0.24 g |
| KH$_2$PO$_4$ | 0.50 g |
| KCl | 0.20 g |
| MgCl$_2$ 6H$_2$O | 0.10 g |
| CaCl$_2$ | 0.02 g |
| Trishydroxymethylaminomethane | 6.10 g |
| Casamino acids* | 10.00 g |
| NaCl | 2.50 g |
| L-cysteine | 40.00 mg |
| FeSO$_4$7H$_2$O | 10.00 mg |
| Ascorbic acid | 20.00 mg |
| Reduced glutathion | 100.00 mg |
| Niacin | 4.00 mg |

*or corresponding peptides prepared by enzymatic hydrolysis of casein.

The preculture is effected in the modified SS medium containing or not a cyclodextrin.

The culture, properly speaking, is carried out by seeding a fermentor with a germ concentration in the order of $10^8$ or $10^9$ germs/ml. The germ concentration is evaluated by reading the optical density by spectrophotometric analysis at 650 nm.

The culture medium in the fermentor is a modified SS medium containing a cyclodextrin at a concentration of 1.7 g/liter.

The culture is carried out at 35–°37° C., and preferably at 36° C. with stirring and with aeration.

The etherified derivative of D-glucose polymer employed in a cellulose having an average molecular weight of 9,300 and whose certain alcohol groups have been methylated (% of substitution: about 30% by weight).

When the addition of methylcellulose is carried out all at once, the amount added is, preferably, about 0.1 g/liter. This addition can be made when the germ is in the exponential growth phase, generally after 24 hours of culture.

When the addition is carried out over several stages, the total amount added is also, preferably, 0.1 g/liter.

The methylcellulose solution can be added in 4 stages, for example after 7 hours, 24 hours, 33 hours and 38 hours of culture.

The evolution of the biomass is estimated by measuring during the course of time the optical density at 650 nm and by measuring the opacity using a standard OMS equivalent to 10 "Opacity units" per ml, a unit corresponding to a billion germs/ml.

The amount of pertussis toxin antigens and F-BA in the supernatant is estimated by an ELISA test using anti-F-HA antibodies and anti-pertussis toxin antibodies purified by immunoaffinity starting with hyperimmunized sera, respectively, of goat and donkey.

The duration of the culture operation depends on the microbial development and expression in the culture supernatant of pertussis toxin and F-HA. This period lasts between 30 and 72 hours, and more often between 40 and 45 hours.

The following non-limiting examples are given to illustrate the invention.

EXAMPLE 1

In order to illustrate the favorable effect of the culture medium composition of the present invention with regard to the development of B. pertussis phase I and on the production in the culture medium of pertussis toxin antigens and F-HA, a comparative study of the following medium formulations has been (1) modified Stainer and Scholte medium, i.e. medium I as defined above (supplied with caseine hydrolyzate);
(2) medium A=modified Stainer and Scholte medium containing β-cyclodextrin at a concentration of 1.67 g/liter;
(3) modified Stainer and Scholte medium containing B-2,6-di0-methyl cyclodextrin at a final concentration of 1.67 g/liter (medium defined by A. Imaizumi, Y. Suzuki, S. Ono, H. Sato and Y. Sato (1983) J. Clin. Microbiol., 17, No. 5, 781-786); and
(4) medium B=identical to medium A with controlled additions of type A15 methylcellulose sold by Colorcon, as described above.

These media are analyzed in a fermentor having a useful capacity of 30 liters with B. pertussis phase I Tohama strain.

These cultures are carried out under identical fermentation conditions (stirring, aeration, pH, duration and the like).

At regular intervals the biomass and the amount of pertussis toxin and F-HA in the supernatant are evaluated.

The results are indicated in FIGS. 1, 2 and 3.

FIG. 2 represents the evolution in time of the production of F-HA as a function of the culture medium composition; and FIG. 3 represents the evolution in time of the production of pertussis toxin as a function of the culture medium.

Figure 1:
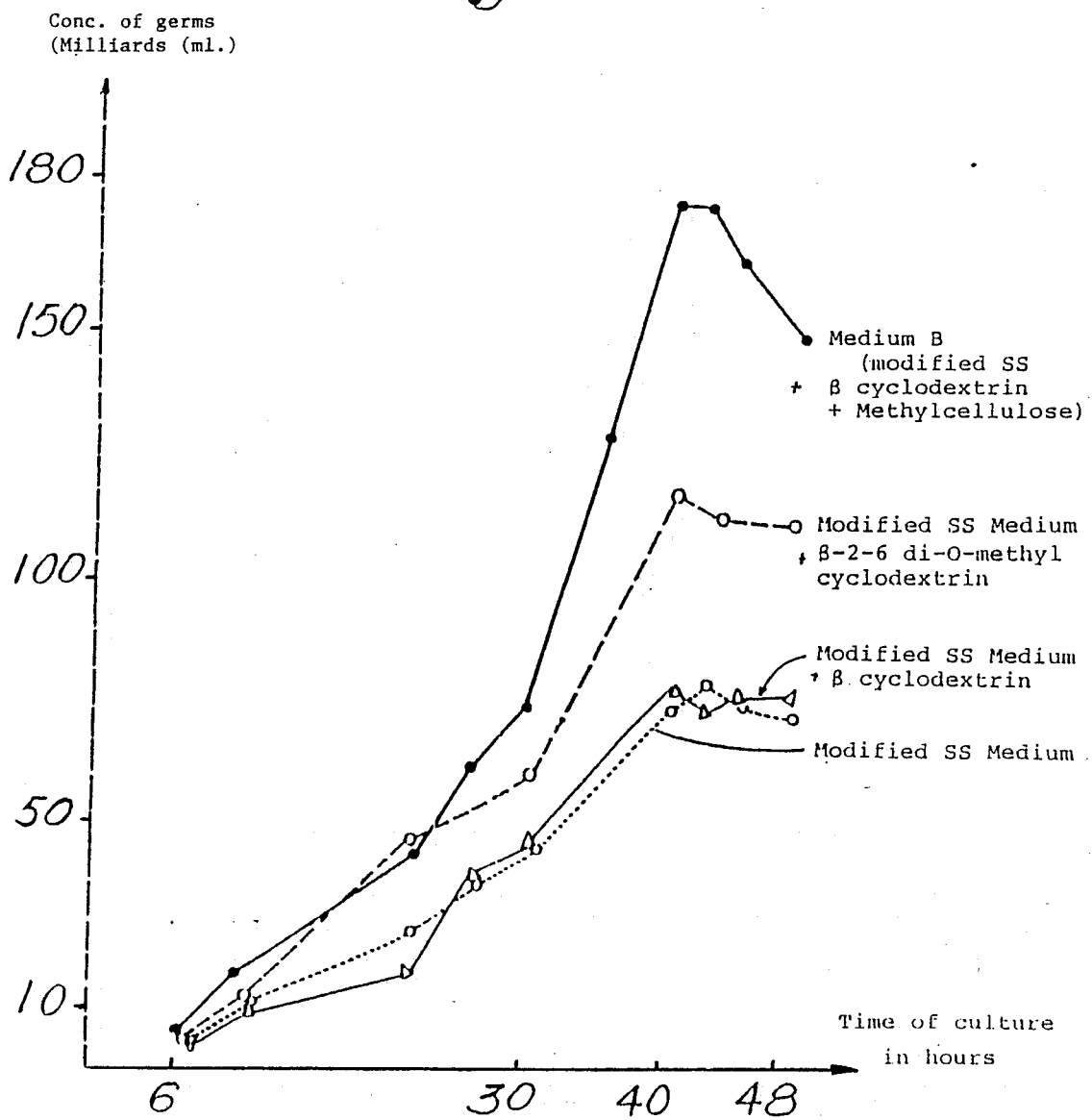
FIG. 1 represents the evolution in time of the biomass as a function of the culture medium composition.

From an analysis of the resulting curves it is apparent that:

The single addition of β-cyclodextrin to the Stainer and Scholte medium did not increase the biomass, nor the production of pertussis toxin antigens and F-HA. In the medium and under the fermentation conditions employed (with stirring) there is no production of F-HA in the culture medium.

On the other hand, the substitution of the β-cyclodextrin by its 2,6-di-0-methyl derivative favors the microbial development and the production of pertussis toxin and F-HA.

Finally, medium B (with the addition of methylcellulose) increases even more the biomass and the production of pertussis toxin and F-HA in the medium.

The Tohama strain is a strain filed with the Institute for Fermentation Collection, Osaka, Japan, under No. IFO-14073.

Moreover, it is available in the Japanese Federation of Culture Collection of Microorganisms, Institute of Medical Science, University of Tokyo, Shirojanedai-461, Milato-ku, Tokyo 108, Japan.

EXAMPLE 2

In order to evaluate the influence of various derivatives of cellulose on the development of the biomass and on the expression of pertussis toxin antigens and F-HA in the supernatant of the culture, a series of tests of culture in Erlenmeyer flasks have been carried out.

Using two ampoules of lyophilized B. pertussis phase I Tohama strain, 8 tubes containing the solid Bordet-Gengou medium were seeded. After incubation for 68 hours at 36° C., in a humid atmosphere, each tube is taken up in about 25 ml of medium A such as defined in Example 1 (modified SS with β-cyclodextrin). The resulting germ suspension is employed to seed 4 2-liter Erlenmeyer flasks containing 500 ml of medium A. The flasks are incubated for 24 hours at 36° C. with stirring.

The bacterial suspensions are combined and the mixture is used to seed 18 2-liter Erlenmeyer flasks including 450 ml of medium A. They are incubated with stirring for 48 hours. At the end of 24 hours, each series of 2 flasks receives 25 ml of a solution containing 1.25 g/liter of one of the cellulose derivatives indicated in Table I, below.

After 42 hours of culture, the pertussis toxin and F-HA concentration in each medium tested is determined by immunoenzymatic method. The results are set forth in Table I.

TABLE I

| Cellulose derivative added to Medium A | Tox. pertussis ELISA/ml units | F-HA ELISA/ml units |
| --- | --- | --- |
| Control - Medium A, alone | 12 | 50 |
| Methocel A15 | 50 | 1560 |
| Methocel A4C | 25 | 825 |
| Methocel A4M | 25 | 325 |
| Methocel E5 | ND | 1100 |
| Methocel E15 | 15 | 1562 |

TABLE I-continued

| Cellulose derivative added to Medium A | Tox. pertussis ELISA/ml units | F-HA ELISA/ml units |
| --- | --- | --- |
| Methocel E4M | 27 | 1100 |
| Carboxymethyl cellulose: | | |
| A Kucel AF 2805 | 17 | 50 |
| AF 2205 | 20 | 50 |

The methylated derivatives of cellulose type methocel A15, A4C and A4M sold by Colorcon have a very favorable influence on the production of pertussis toxin antigens and F-HA. The amount of pertussis toxin in the culture medium, after 42 hours of culture, is 2–4 times greater than that obtained with medium A and with regard to the concentration of F-HA, it is 6–30 times greater. Under the conditions employed, the better yields are obtained with methylcellulose type A15.

The carboxymethylated derivatives have a favorable effect on the expression of pertussis toxin. The production of pertussis toxin is, however, less high than that obtained using methylated derivatives of cellulose. On the other hand, under the conditions studied, the carboxymethylated derivatives of cellulose have no influence on the production of F-HA.

EXAMPLE 3

This example describes the fermentation process of Bordetella pertussis phase I Tohama strain in medium B (modified SS+β-cyclodexrin+methylcellulose), in a fermentor having a useful volume of 1,000 liters. The purpose of this culture is to produce in the culture supernatant significant amounts of pertussis toxin antigens and F-HA, compatible with the operation on an industrial scale of an acellular anti-whooping cough vaccine compound having highly purified active principles: pertussis anatoxin and/or F-HA.

This industrial culture comprises the following steps:

PRECULTURE 1

Tubes containing the solid Bordet-Gengou medium are seeded with B. pertussis phase I Tohama strain.

Five lyophilized ampoules, each taken up by 1 ml of soy trypticase medium are used to seed 30 tubes containing the Bordet-Gengou medium. The tubes are placed in an oven at 36° C. under a humid atmosphere for 60 hours.

PRECULTURE 2

Each tube is taken up by about 25 ml of medium A. After checking the purity by the Gram test, the recovered germ suspensions ar admixed. The mixture is used to seed 16 2-liter Erlenmeyer flasks, each containing 400 ml of medium A. Each flask receives about 50 ml of the mixture of the germ suspension. The flasks are incubated at 36° C. for 24 hours with shaking-type stirring.

After examination of the purity of the flasks by the Gram test and checking for the absence of contaminant development on the Bordet-Gengou media, the bacteria suspensions of the flasks are combined and the germ concentration is estimated by measuring the optical density at 650 nm. Preculture 2: $OD_{650nm} = 1.80$ corresponding to about $40 \times 10^9$ germs/ml.

PRECULTURE 3: Prefermentor stage

Two fermentors having a capacity of 40 liters of medium A are each seeded with 3.2 liters of the preceding preculture, so as to have a germ suspension titrating at least 10% germs/ml The culture is carried out at 36° C., with moderate stirring and under aeration for 24 hours.

At the end of the fermentation, the purity is checked by the Gram test and the germ density is determined by measuring the optical density at 650 nm. After 24 hours of incubation the optical densities measured on each prefermentor were equal to 3.01 and 3.37, which corresponds to a bacteria concentration of about $64-68 \times 10^9$ germs/ml.

INDUSTRIAL CULTURE

An industrial culture was carried out in a fermentor containing 1,000 liters of medium B as defined in Example 1. This fermentor was seeded with the preceding preculture.

The germ concentration after seeding is in the order of $5 \times 10^9$ germs/ml The culture is carried out at 35° C., with stirring for 40 hours, with aeration.

During the course of the fermentation there is added in several stages a solution of methylcellulose of the Colorcon A15 type, as a function of the evolution of the biomass over the course of time. The methylcellulose additions were carried out at the end of the 7th, 24th and 32nd hour of culture. Each addition consisted in transferring in the fermentor 24 liters of a solution of medium A containing 1.25 g/liter of methylcellulose.

Culturing was stopped at t=40 hours.

After cooling the culture was inactivated by the addition of merthiolate at a final concentration of 0.01% (P/V), and centrifuged continuously.

The supernatant was clarified by filtration. The evolution of the biomass, as well as the amount of antigens (measured by an ELISA test) in the culture supernatant, over the course of time, are set forth in Table II below.

TABLE II

| Culture Time | $OD_{650}$ | Germ conc. in ml | Amount of F-HA ELISA units/ml | Amount of pertussis toxin, ELISA units per ml |
|---|---|---|---|---|
| t = 0 | 0.301 | $7.5 \times 10^9$ | | |
| t = 6 hrs | 0.77 | $15 \times 10^9$ | | |
| t = 22 hrs | 3.54 | $72 \times 10^9$ | | |
| t = 24 hrs | 4.10 | $90 \times 10^9$ | 450 | 240 |
| t = 30 hrs | 5.97 | $120 \times 10^9$ | 1800 | 480 |
| t = 40 hrs | 8.20 | $170 \times 10^9$ | 2200 | 550 |

EXAMPLE 4: Culture of *Bordetella bronchiseptica*

The *Bordetella bronchiseptica* strain was ATCC14455.

Comparative cultures were made with the following culture media:

Medium I: modified SS medium as defined in the specification above;

Medium A: modified SS medium + beta-cyclodextrin, as defined in example 1;

Medium B: identical to medium A + 0.1 g/l of A15 methylcellulose.

The culture with medium B further comprised three additions of A15 methylcellulose, up to a total concentration of about 0.2 g/l after the last addition.

In order to mimic an industrial fermentation process, three precultures were first carried out.

The fermentation steps were as follows:

PRECULTURE 1:

One lyophilized ampoule of β-bronchiseptica was used for seeding 10 Petri boxes containing Bordet Gengou solid medium. The cultures were incubated 37° C. for 72 hours.

PRECULTURE 2:

The content of 2 Petri boxes was taken up by some ml of medium I, and this was used seeding four 1-liter flasks each containing 200ml of medium I.

The cultures were incubated at 37° C. under agitation for 24 hours.

PRECULTURE 3:

12 ml of preculture 2 were used for seeding four 2-liter flasks containing 400 ml of medium I.

The cultures were incubated at 37° C. under agitation.

During the course of the fermentation, there was added (three times) into the flasks containing medium B, at intervals, a solution of methylcellulose (A15). The methylcellulose additions were carried out at the end of the 6th, 24th and 29th hour of culture. Each addition consisted in adding 44 ml of medium A containing 1.25 g/l of methylcellulose.

At various time intervals, the optical density at 650 nm of 10 ml samples was measured, and after centrifugation of the samples, the FHA content of the supernatant was determined by ELISA; the results are summarized in Table III.

TABLE III

| Culture Time (Hours) | OD 650 | | | FHA Content (ELISA arbitrary units/ml) | | |
|---|---|---|---|---|---|---|
| | Medium I | A | B | I | A | B |
| 0 | 0.14 | 0.14 | 0.14 | 0 | 0 | 0 |
| 6 | 1.0 | 1.0 | 1.0 | 0 | 0 | 0 |
| 26 | 4.8 | 4.2 | 7.8 | 104 | 78 | 511 |
| 36 | 4.2 | 4.3 | 6.8 | 43 | 131 | 518 |

What is claimed is:

1. A culture medium composition for bacteria of the Bordetella genus comprising a nutrient medium containing cyclodextrin or a derivative thereof and at least one etherified derivative of D-glucose polymer having a molecular mass of at least 2,000.

2. The composition of claim 1 wherein said etherified derivative of D-glucose is a cellulose derivative having a portion of the hydroxyl groups thereof etherified by lower alkyl or hydroxyloweralkyl groups.

3. The composition of claim 2 wherein said etherified derivative of D-glucose is selected from the group consisting of methylcellulose, hydroxypropyl methylcellulose, hydroxyethyl cellulose and hydroxybutyl cellulose.

4. The composition of claim 1 wherein said etherified derivative of D-glucose is carboxymethyl cellulose 5. The composition of claim 1 wherein said etherified derivative of D-glucose is present in an amount ranging from 0.01 to 2 g/liter of said composition.

6. The composition of claim 5 wherein said etherified derivative of D-glucose is present in an amount ranging from 0.05 to 0.5 g/liter of said composition.

7. The composition of claim 1 wherein said cyclodextrin, or a salt thereof, is present in an amount ranging from 0.5 to 5 g/liter of said composition.

8. The composition of claim 7 wherein said cyclodextrin, or a salt thereof, is present in an amount ranging from 1 to 2 g/liter of said composition.

9. A process for culturing bacteria of the Bordetella genus comprising cultivating said bacteria in a nutrient medium containing cyclodextrin or a salt thereof and at least one etherified derivative of D-glucose polymer having a molecular mass of at least 2,000.

10. The process of claim 9, wherein said etherified derivative of D-glucose is added to the medium in several stages, the total amount of said etherified derivative being added ranging from 0.05 to 2 g/liter.

11. The process of claim 10 wherein said etherified derivative of D-glucose is added to the medium in several stages, the total amount of said etherified derivative being added ranging from 0.5 to 0.5 g/liter.

* * * * *

UNITED STATES PATENT AND TRADEMARK OFFICE
CERTIFICATE OF CORRECTION

PATENT NO. : 4,965,205
DATED : October 23, 1990
INVENTOR(S) : QUENTIN-MILLET et al It is certified that error appears in the above-identified patent and that said Letters Patent is hereby corrected as shown below:

TITLE PAGE

Insert --

[30] Foreign Application Priority Data

March 27, 1986  France  86 0440--.

Signed and Sealed this

Tenth Day of May, 1994

*Attest:*

BRUCE LEHMAN

*Attesting Officer*   *Commissioner of Patents and Trademarks*